United States Patent
Hattori et al.

(10) Patent No.: US 7,382,124 B2
(45) Date of Patent: Jun. 3, 2008

(54) APPARATUS FOR PRODUCING HYPERPOLARIZED NOBLE GAS, AND NUCLEAR MAGNETIC RESONANCE SPECTROMETER AND MAGNETIC RESONANCE IMAGER WHICH USE HYPERPOLARIZED NOBLE GASES

(75) Inventors: Mineyuki Hattori, Tokyo (JP); Takashi Hiraga, Osaka (JP); Tatsuya Asanuma, Osaka (JP)

(73) Assignee: National Institute of Advanced Industrial Science and Technology (JP)

( * ) Notice: Subject to any disclaimer, the term of this patent is extended or adjusted under 35 U.S.C. 154(b) by 37 days.

(21) Appl. No.: 11/435,138

(22) Filed: May 16, 2006

(65) Prior Publication Data

US 2006/0263300 A1 Nov. 23, 2006

(30) Foreign Application Priority Data

May 18, 2005 (JP) .......................... P2005-146029

(51) Int. Cl.
*G01V 3/00* (2006.01)
*A61B 5/055* (2006.01)

(52) U.S. Cl. ...................... 324/304; 324/321; 324/318; 600/411; 600/420

(58) Field of Classification Search ........ 324/318–322; 62/49.1; 600/420
See application file for complete search history.

(56) References Cited

U.S. PATENT DOCUMENTS

| | | | |
|---|---|---|---|
| 5,545,396 A * | 8/1996 | Albert et al. ................. | 424/9.3 |
| 5,642,625 A * | 7/1997 | Cates et al. .................. | 62/55.5 |
| 6,269,648 B1 * | 8/2001 | Hasson et al. ................ | 62/3.1 |
| 6,430,939 B2 * | 8/2002 | Hasson et al. ................ | 62/49.1 |
| 6,566,875 B1 * | 5/2003 | Hasson et al. ............... | 324/309 |
| 6,648,130 B1 * | 11/2003 | Hasson et al. ................ | 206/0.7 |
| 6,807,810 B2 * | 10/2004 | Hasson et al. ................. | 62/3.1 |
| 6,995,641 B2 * | 2/2006 | Hasson et al. ............... | 335/301 |
| 7,066,319 B2 * | 6/2006 | Hasson et al. ................ | 206/0.7 |
| 2001/0025493 A1 * | 10/2001 | Hasson et al. ................. | 62/3.1 |

(Continued)

FOREIGN PATENT DOCUMENTS

JP 2003-245263 9/2003

OTHER PUBLICATIONS

Moyoko Saito, Takashi Hiraga, Hineyuki Hattori and Toshiharu Nakai, "An investigation of the pipeline materials for continuous hyperpolarized 129 Xegas imaging," Proceedings of the International Society for Magnetic Resonance in Medicine, vol. 12 (May 2004), p. 1685.

*Primary Examiner*—Brij Shrivastav
*Assistant Examiner*—Tiffany A. Fetzner
(74) *Attorney, Agent, or Firm*—Ostrolenk, Faber, Gerb & Soffen, LLP

(57) ABSTRACT

This apparatus for producing a hyperpolarized noble gas includes: a hyperpolarized noble gas generating cell in which a noble gas is subjected to an optical pumping in the presence of an alkali metal so as to generate a hyperpolarized noble gas; and a very fine capillary tube having an inside diameter of 0.1 to 1.25 mm which is positioned downstream from the hyperpolarized noble gas generating cell. This nuclear magnetic resonance spectrometer includes the above apparatus for producing a hyperpolarized noble gas and a nuclear magnetic resonance measuring instrument. This magnetic resonance imager includes the above apparatus for producing a hyperpolarized noble gas and a magnetic resonance image measuring instrument.

3 Claims, 5 Drawing Sheets

U.S. PATENT DOCUMENTS

2002/0196116 A1* 12/2002 Hasson et al. .............. 335/304
2003/0189182 A1* 10/2003 Hasson et al. ........... 251/129.2
2004/0065563 A1*  4/2004 Hasson et al. ............... 206/0.7
2006/0118430 A1*  6/2006 Hasson et al. ............... 206/0.7
2006/0263300 A1* 11/2006 Hattori et al. ............... 424/9.3

* cited by examiner

US 7,382,124 B2

APPARATUS FOR PRODUCING HYPERPOLARIZED NOBLE GAS, AND NUCLEAR MAGNETIC RESONANCE SPECTROMETER AND MAGNETIC RESONANCE IMAGER WHICH USE HYPERPOLARIZED NOBLE GASES

BACKGROUND OF THE INVENTION

1. Field of the Invention

The present invention relates to an apparatus for producing a hyperpolarized noble gas, a nuclear magnetic resonance spectrometer using a hyperpolarized noble gas, and a magnetic resonance imager using a hyperpolarized noble gas.

This application claims priority from Japanese Patent Application No. 2005-146029 filed on May 18, 2005, the content of which is incorporated herein by reference.

2. Background Art

Gases at atmospheric pressure have a lower atomic density than liquids and solids, and until recently had not been used as the "targets" in nuclear magnetic resonance spectroscopy (NMR) or magnetic resonance imaging (MRI).

However, when the vapor of an alkali metal such as rubidium (Rb), cesium (Cs) or the like and a noble gas composed of monatomic molecules having a nuclear spin with a spin quantum number of 1/2 such as the xenon isotope having a mass number of 129 ($^{129}$Xe), the helium isotope having a mass number of 3 ($^{3}$He) or the like are placed together and are irradiated with a circularly polarized laser to excite the electron spin system (a process called "optical pumping"), the spin system of the noble gas can be polarized (this is known to as "hyperpolarization").

It has been reported that the NMR signal intensity is enhanced several 10,000-fold in this way, enabling NMR signals to be obtained which are more than 100 times stronger than when the same volume of water is used. This report has drawn attention to NMR/MRI techniques that use hyperpolarized noble gases (see, for example, Patent Document 1).

Here, "hyperpolarization" signifies that the distribution in the spin numbers which occupy the nuclear spin energy levels of an atomic nucleus corresponding to the orientation state with respect to a main static magnetic field is extremely polarized compared with the distribution under a state of thermal equilibrium (Boltzmann distribution).

The process of forming a hyperpolarized noble gas is generally called optical pumping, and works as follows. When an electron at the ground state level of rubidium, for example, is excited by light absorption, jumps to an excited state level, and then returns to the ground state level, it transits with high probability to one of the electron levels of the rubidium ground state levels of which degeneracy has been magnetically broken by an externally applied magnetic field, thereby creating a state of high electron spin polarization in the rubidium molecule. When this rubidium having a highly polarized state collides with a noble gas such as xenon or the like, the highly polarized state of the rubidium is transferred to the nuclear spin system of the noble gas such as xenon or the like, resulting in a hyperpolarized noble gas.

Specifically, as shown in FIG. 5, the nuclear spin energy levels of $^{129}$Xe are split by optical pumping, giving rise to an unequal distribution in the number of occupied spin (difference in the number of occupied spin). The magnetic field which is externally applied at the time of such optical pumping is a low magnetic field of about $10^{-2}$ T (tesla) (100 gauss). This hyperpolarized $^{129}$Xe, instead of being used to carry out measurement in this state, is introduced to a nuclear magnetic resonance spectrometer or a magnetic resonance imager at an even higher magnetic field of about 0.3 T. Thus, the resonance frequency between the two energy levels can be increased with the difference in the number of occupied spin being maintained, enabling the NMR detection sensitivity to be enhanced.

In an NMR/MRI process which uses a hyperpolarized noble gas, unlike an ordinary prior-art NMR/MRI process, measurement does not necessarily involve the integration of NMR signals. Therefore, because the NMR signals are measured only once, it is desirable to supply the hyperpolarized noble gas generated by optical pumping in a hyperpolarized noble gas generating cell to the NMR spectrometer or the magnetic resonance imager in a state in which the difference in the number of occupied spin is maintained.

The phenomenon in which the difference in the number of occupied spin of the hyperpolarized noble gas decreases and approaches the Boltzmann distribution is called "spin relaxation." The spin relaxation is undesirable because when it occurs, the NMR signal intensity decreases. The main cause of the spin relaxation is thought to be the distortion of electron clouds in the hyperpolarized noble gas due to collisions with the inside wall of the cell or the gas pipeline.

We thus investigated materials of a pipe connected on the downstream side of the hyperpolarized noble gas generating cell, using pipes having an inside diameter of 7 mm. As a result, we found that a Pyrex (trademark) glass pipe is better than a stainless steel pipe or a surface-treated stainless steel pipe because it does not readily give rise to spin relaxation, and we reported our findings (See, for example, Non-Patent Document 1).

However, even with the use of a Pyrex (trademark) glass pipe having an inside diameter of 4 mm, the distance for which the hyperpolarized noble gas can be supplied without allowing spin relaxation to arise is at best somewhat under 1 meter. Hence, it was not possible to supply the hyperpolarized noble gas over a long distance.

In particular, in the case in which a superconducting magnet having a large magnetic field, for example, is used in the NMR spectrometer or the magnetic resonance imager, there is a large leakage magnetic field from the superconducting magnet. This leakage magnetic field apparently has an adverse effect on the hyperpolarized noble gas generating cell located upstream, which lowers the amount of hyperpolarized noble gas generated. Accordingly, it is necessary to have the distance between the hyperpolarized noble gas generating cell and the NMR spectrometer or the magnetic resonance imager be at least 1 m, and preferably 2 to 3 m or more.

Moreover, a glass pipe having an inside diameter of about 4 to 7 mm is more fragile to impacts than a stainless steel pipe, and thus more subject to failure. This, combined with the fact that it cannot be bent, makes it inconvenient to handle for a long-distance supply of the hyperpolarized noble gas.

It is therefore an object of the present invention to provide an apparatus for producing a hyperpolarized noble gas which inhibits spin relaxation and avoids a decline in the NMR signal intensity of the hyperpolarized noble gas even when the gas is supplied over a long distance. Another object of the invention is to provide a nuclear magnetic resonance spectrometer using a hyperpolarized noble gas which includes such an apparatus for producing a hyperpolarized noble gas. A further object of the invention is to provide a magnetic resonance imager using a hyperpolarized noble gas which includes such an apparatus for producing a hyperpolarized noble gas.

(Patent Document 1) Japanese Patent Application, First Publication No. 2003-245263

(Non-Patent Document 1) Moyoko Saito, Takashi Hiraga, Hineyuki Hattori and Toshiharu Nakai, "An investigation of the pipeline materials for continuous hyperpolarized $^{129}$Xe gas imaging," Proceedings of the International Society for Magnetic Resonance in Medicine, Vol. 12 (May 2004), p. 1685

SUMMARY OF THE INVENTION

The apparatus for producing a hyperpolarized noble gas of the invention includes a hyperpolarized noble gas generating cell in which a noble gas is subjected to an optical pumping in the presence of an alkali metal so as to generate a hyperpolarized noble gas, and a very fine capillary tube having an inside diameter of 0.1 to 1.25 mm which is positioned downstream from the hyperpolarized noble gas generating cell.

The nuclear magnetic resonance spectrometer of the present invention, which uses a hyperpolarized noble gas, includes the apparatus for producing a hyperpolarized noble gas of the present invention and a nuclear magnetic resonance measuring instrument.

The magnetic resonance imager of the present invention, which uses a hyperpolarized noble gas, includes the apparatus for producing a hyperpolarized noble gas of the present invention and a magnetic resonance image measuring instrument.

In accordance with the apparatus for producing a hyperpolarized noble gas of the present invention and both the nuclear magnetic resonance spectrometer of the present invention and the magnetic resonance imager of the present invention which use a hyperpolarized noble gas have a very fine capillary tube with an inside diameter of 0.1 to 1.25 mm positioned downstream from the hyperpolarized noble gas generating cell. By using this very fine capillary tube to supply a hyperpolarized noble gas, the volume within the tube is reduced, which allows the hyperpolarized noble gas to be passed through the tube at an increased transfer rate per unit volume, reducing collisions with the inner wall of the tube. Spin relaxation is thus suppressed, making it possible to prevent a decline in the NMR signal intensity even though the supply distance is a long distance of about 1 to 22 m.

A very fine capillary tube having an inside diameter of 0.1 to 1.25 mm can be bent and is also resistant to impact. Therefore, by using a very fine capillary tube having an inside diameter of 0.1 to 1.25 mm, cracking and rupture due to impacts are prevented, which facilitates handling.

The nuclear magnetic resonance spectrometer of the present invention and the magnetic resonance imager of the present invention, which use a hyperpolarized noble gas, are able to supply the hyperpolarized noble gas over a long distance, enabling the equipment to be installed in such a way that a considerable distance is placed between the hyperpolarized noble gas generating cell and the nuclear magnetic resonance spectrometer or the magnetic resonance imager. As a result, the effects of the leakage magnetic field from the nuclear magnetic resonance spectrometer or the magnetic resonance imager on the hyperpolarized noble gas generating cell can be minimized. The amount of hyperpolarized noble gas generated is thus enhanced, enabling the NMR signal intensity to be increased.

The nuclear magnetic resonance spectrometer of the present invention and the nuclear magnetic imager of the present invention, which use a hyperpolarized noble gas, can be employed for diagnosis of the respiratory organs and the brains in humans and animals.

DESCRIPTION OF THE PREFERRED EMBODIMENTS

A nuclear magnetic resonance spectrometer which uses a hyperpolarized noble gas and includes an apparatus for producing a hyperpolarized noble gas in accordance with a preferred embodiment of the present invention is described in detail below in conjunction with the diagrams.

Figure 1:
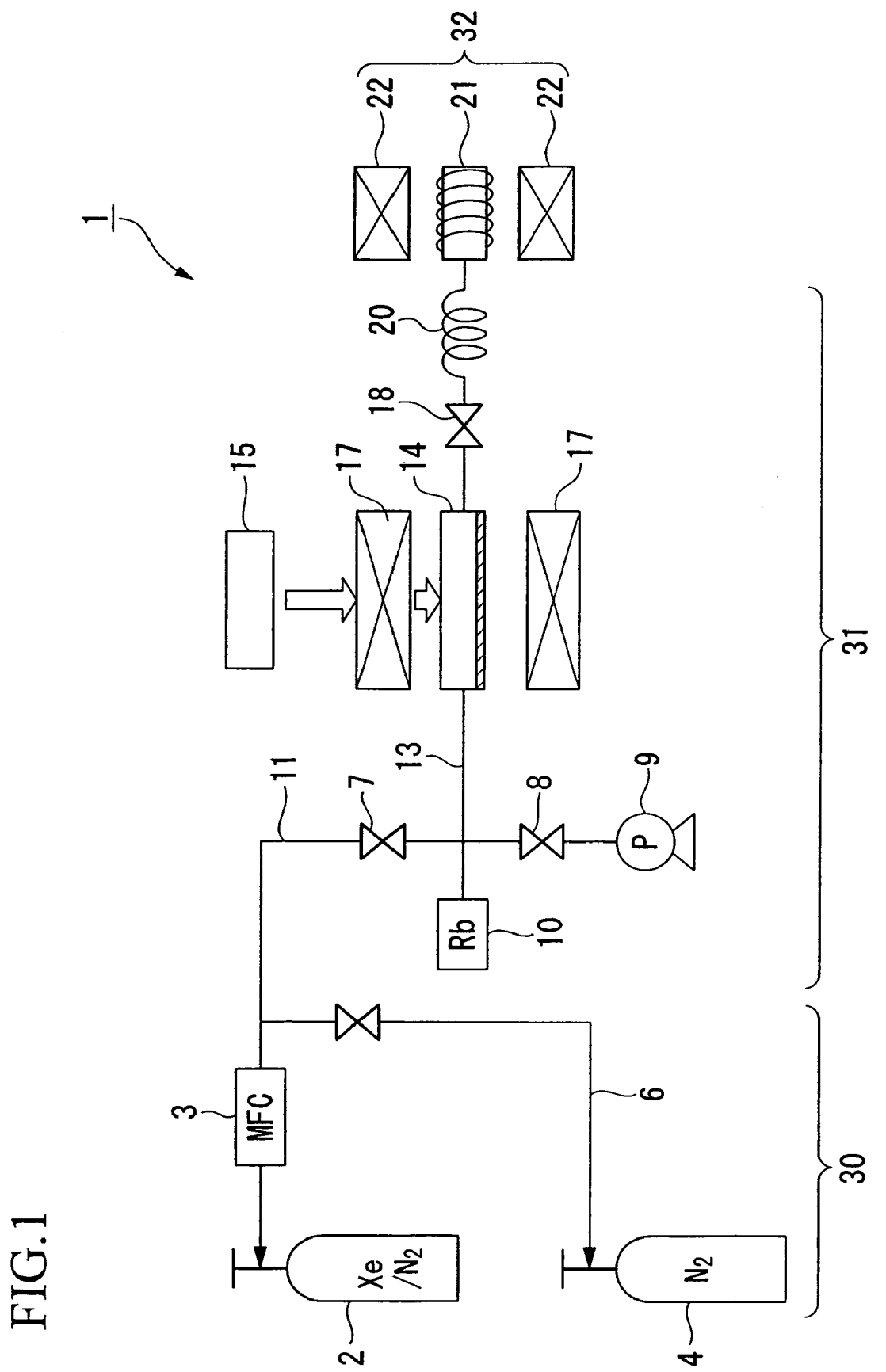
FIG. 1 is a schematic view of the configuration of a nuclear magnetic resonance spectrometer using a hyperpolarized noble gas which includes an apparatus for producing a hyperpolarized noble gas of one embodiment of the present invention.
Figure 2:
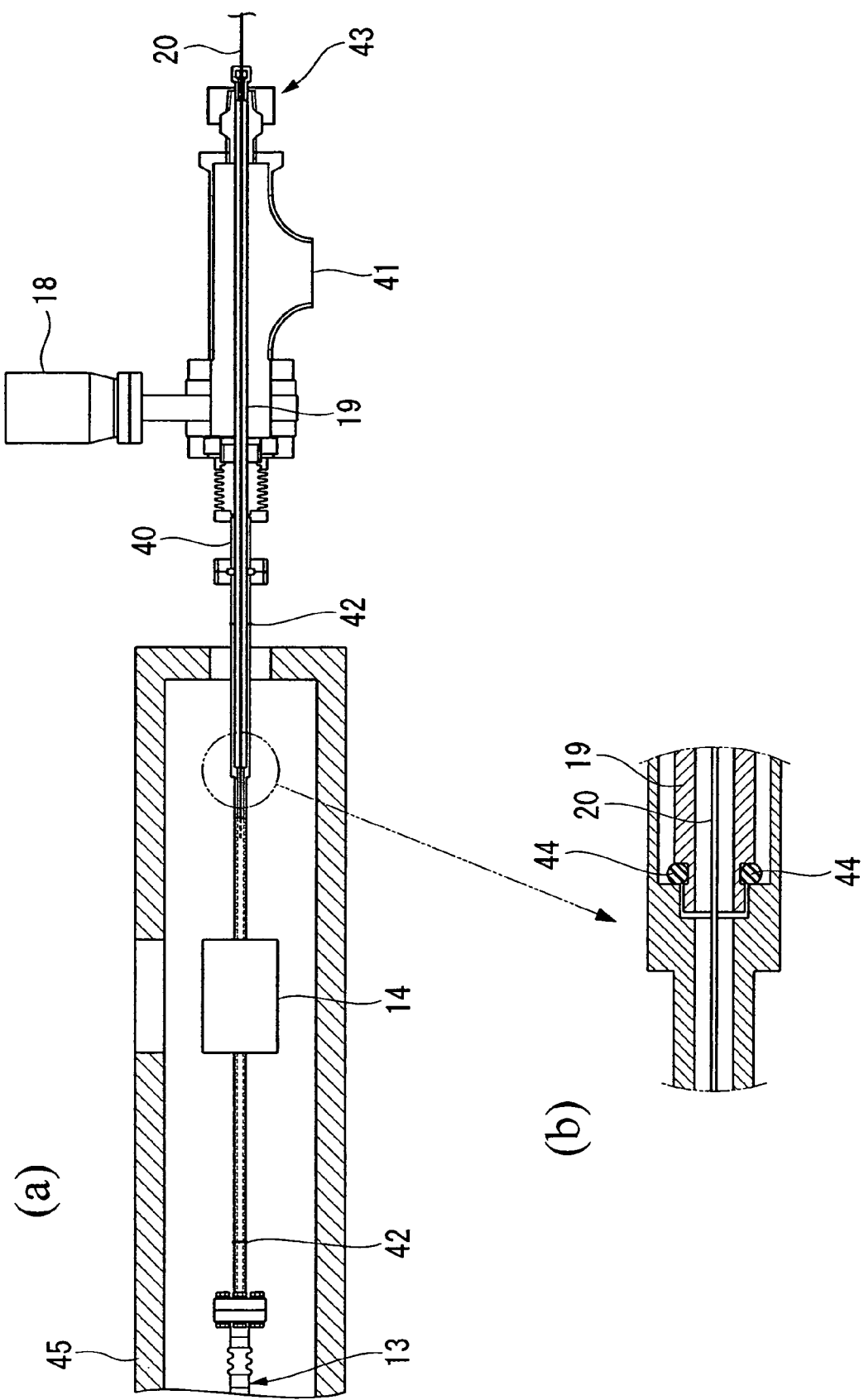
FIG. 2 (a) is an enlarged sectional view of the area including the hyperpolarized noble gas generating cell and the end portion of the very fine capillary tube in the apparatus for producing a hyperpolarized noble gas of the one embodiment of the present invention, and FIG. 2 (b) is an enlarged view of a region within a two-dot chain circular line in FIG. 2 (a).

FIG. 1 is a schematic view of the configuration of a nuclear magnetic resonance spectrometer 1 using a hyperpolarized noble gas which includes a hyperpolarized noble gas generator 31 (an apparatus for producing a hyperpolarized noble gas) of one embodiment of the present invention. FIG. 2 (a) is an enlarged sectional view of the area including the hyperpolarized noble gas generating cell 14 and the end portion of the very fine capillary tube 20 in the hyperpolarized noble gas generator 31 of the present embodiment of the present invention.

The nuclear magnetic resonance spectrometer 1 using a hyperpolarized noble gas of the present embodiment primarily includes a noble gas supply unit 30, the hyperpolarized noble gas generator 31, and a nuclear magnetic resonance measuring instrument 32.

The noble gas supply unit 30 supplies a noble gas serving as the feedstock to the hyperpolarized noble gas generator 31. In this embodiment, by using a noble gas cylinder 2 and a mass flow controller 3 connected thereto, a noble gas can be fed through a noble gas feed line 111 to the hyperpolarized noble gas generating cell 14 at a flow rate of 5 to 100 sccm, preferably 10 to 30 sccm, and most preferably 15 sccm.

In addition, a nitrogen gas feed line 6 for purging and a nitrogen gas cylinder 4 are connected to the noble gas feed line 11 so as to enable the noble gas supply unit 30 and the hyperpolarized noble gas generator 31 to be cleaned and purged.

The hyperpolarized noble gas generator 31 primarily includes an alkali metal storage container 10, the hyperpolarized noble gas generating cell 14, optical pumping magnets 17, 17, an optical pumping excitation light source 15, and a very fine capillary tube 20.

The noble gas supply unit 30 and the alkali metal storage container 10 are connected upstream of the hyperpolarized noble gas generating cell 14 in such a way as to enable the alkali metal serving as the optical pumping medium and the noble gas serving as the feedstock to each be separately introduced into the hyperpolarized noble gas generating cell 14.

The optical pumping excitation light source 15 and the optical pumping magnets 17, 17 are disposed laterally in the lengthwise direction of the hyperpolarized noble gas generating cell 14 in such a way as to enable the noble gas to be hyperpolarized by irradiating the interior of the hyperpolarized noble gas generating cell 14 with light while at the same time applying a magnetic field.

Referring to FIG. 2 (a), downstream from the hyperpolarized noble gas generating cell 14, the very fine capillary tube 20 is inserted such that the end portion thereof is located at the interior of a glass tube which is connected to the downstream end of the hyperpolarized noble gas generating cell 14, via a guiding glass tube 19 in a protective line 40, in such a way as to enable the hyperpolarized noble gas to be supplied to the nuclear magnetic resonance measuring instrument 32. In addition, a gate valve 18 is connected to the protective line 40 so that, when the alkali metal is introduced to the hyperpolarized noble gas generating cell 14, the guiding glass tube 19 and the very fine capillary tube 20 can be removed and the line can be opened and closed.

The alkali metal storage container 10 is a cylindrical or rectangular stainless steel receptacle of a size that is capable of accommodating at the interior a glass ampule which encapsulates therein the alkali metal. A line 13 is connected to one end of the alkali metal storage container 10 so as to enable the alkali metal to be introduced through the line 13 to the hyperpolarizing noble gas generating cell 14.

In addition, this line 13 has a vacuum pump 9 connected thereto through a valve 8. Hence, by removing the guiding glass tube 19 and the very fine capillary tube 20 and closing the gate valve 18, a vacuum can be pulled with the vacuum pump 9 on the alkali metal storage container 10, the line 13, and the interior of the hyperpolarized noble gas generating cell 14.

As shown in FIG. 2 (a), the hyperpolarized noble gas generating cell 14 is a cylindrical, rectangular or tabular glass cell, and glass tubes having an inside diameter of 4 to 6 mm are connected at both ends of the hyperpolarized noble gas generating cell 14. The end of the glass tube on the upstream side is coupled to a metal line by metal-to-glass welding at a spot indicated by the reference symbol 42. Moreover, this metal line is connected through a flange to the stainless steel line 13.

The glass tube on the downstream side provided on the hyperpolarized noble gas generating cell 14 widens out along the length thereof to an inside diameter of 6 to 12 mm, after which it is coupled to a metal line by metal-to-glass welding at a spot indicated by the reference symbol 42. This metal line is, in turn, connected through a flange to the stainless steel protective line 40 and the gate valve 18.

The glass used in the hyperpolarized noble gas generating cell 14 is preferably Pyrex (trademark) glass or silica glass. The hyperpolarized noble gas generating cell 14 may be made of metal, although it is necessary in such a case to provide a window so that light from the optical pumping excitation light source 15 can pass through.

By having the hyperpolarized noble gas generating cell 14 made of glass rather than metal, the alkali metal can be sufficiently irradiated by light from the optical pumping excitation light source 15 and spin relaxation due to collisions between the hyperpolarized noble gas that has formed and the inner wall of the cell can be minimized.

As shown in FIG. 2 (a), a guiding glass tube 19 having an inside diameter of 4 to 7 mm is inserted into the protective line 40 on the downstream side of the hyperpolarized noble gas generating cell 14 and into the gate valve 18. The guiding glass tube 19 has a length of 30 to 40 cm, and passes through the gate valve 18, the protective line 40, and the metal-to-glass weld 42. In addition, as shown in FIG. 2 (b) of the enlarged view of a region within a two-dot chain circular line in FIG. 2 (a), the upstream side end of the guiding glass tube 19 is locked in place with an O-ring 44.

The very fine capillary tube 20 is inserted within the guiding glass tube 19. The upstream side end of the very fine capillary tube 20 passes through the guiding glass tube 19 and is inserted at an insertion length of about 40 to 50 cm into the glass tube provided on the downstream side of the hyperpolarized noble gas generating cell 14. Moreover, the very fine capillary tube 20 does not come into direct contact with the metal line.

By inserting the very fine capillary tube 20 into the guiding glass tube 19 and keeping it from coming into direct contact with the metal line, the generated hyperpolarized noble gas does not collide with the metal wall. This helps to minimize spin relaxation, enabling the hyperpolarized noble gas to be supplied intact to the nuclear magnetic resonance measuring instrument 32.

On the downstream side of the gate valve 18, the guiding glass tube 19 and the very fine capillary tube 20 are locked by a connector 43 in such a way as to support the guiding glass tube 19 and seal the end of the guiding glass tube 19.

The bottom end 41 of the gate valve 18 is connected to a vacuum pump (not shown). This arrangement makes it possible, when the alkali metal is introduced into the hyperpolarized noble gas generating cell 14, to remove the guiding glass tube 19 and the very fine capillary tube 20, close the gate valve 18, and evacuate the line.

Next, as shown in FIG. 2 (a), the hyperpolarized noble gas generating cell 14 is covered by a heating furnace 45 having a window provided in a portion thereof, enabling light from the optical pumping excitation light source 15 to be irradiated through the window and also enabling the hyperpolarized noble gas generating cell 14 to be heated at from room temperature to 300° C.

The very fine capillary tube 20 has an inside diameter of 0.1 to 1.25 mm, preferably 0.2 to 0.8 mm, and more preferably 0.25 to 0.53 mm, and has a length of 1 to 22 m, and preferably 3 to 10 m. It is desirable to use the very fine capillary tube 20 composed of a single tube without joints along its length for inhibiting spin relaxation.

In the case in which the inside diameter of the very fine capillary tube 20 is set to 0.1 to 1.25 mm, the very fine capillary tube 20 is adequately elastic and does not snap when being bent. This prevents the very fine capillary tube 20 from cracking and breaking on impact, and facilitates handling. Moreover, because the interior volume of the very fine capillary tube 20 can be reduced compared with the large-diameter pipelines used in the prior art, it is possible to pass the hyperpolarized noble gas through the tube at a higher transfer rate per unit volume. As a result, collisions of the hyperpolarized noble gas with the inner wall of the very fine capillary tube 20 can be reduced, enabling spin relaxation to be minimized. It is thus possible to supply the hyperpolarized noble gas without lowering the NMR signal intensity even though the supply distance is 1 to 22 m.

The very fine capillary tube 20 may be a commercially available capillary tube made of fused silica, glass or resin such as is commonly employed in gas chromatographs. Among them, the fused silica is preferred from the standpoint of minimizing spin relaxation. Illustrative examples include untreated fused silica capillary tubes (inside diameter: 0.53 mm, 0.25 mm) and inactivated fused silica capillary tubes (inside diameter: 0.53 mm, 0.25 mm) manufactured by GL Sciences, Inc.

Any suitable resin may be employed. However, in the case in which the capillary tube is used in the vicinity of the hyperpolarized noble gas generating cell 14, the ambient temperature is from 150 to almost 200° C. and the capillary tube 20 is rendered strongly alkaline with the alkali metal. Hence, the use of a polycarbonate or a polyimide is preferred.

Optical pumping magnets 17, 17 are disposed above and below the lateral faces of the hyperpolarized noble gas generating cell 14 in the lengthwise direction thereof. By disposing the optical pumping magnets 17, 17 on either side (i.e., above and below) of the hyperpolarizing noble gas generating cell 14, a magnetic field can be applied perpendicular to the direction of gas flow, which is also the lengthwise direction of the hyperpolarized noble gas generating cell 14.

A Helmholtz electromagnet or a permanent magnet having an air-core structure into which light can be passed can be used as the optical pumping magnets 17, 17. The magnetic field generated by the optical pumping magnets 17, 17 is preferably about $0.2 \times 10^{-2}$ to $10 \times 10^2$ T. Even with such a low magnetic field, sufficient noble gas can be hyperpolarized.

In addition, an optical pumping excitation light source 15 is disposed on a lateral side in the lengthwise direction of the hyperpolarized noble gas generating cell 14. A known type of lamp, laser or the like may be used as the optical pumping excitation light source 15. Among them, a laser diode array is preferred because it has a high output and a sharp beam width.

In the case in which the optical pumping excitation light source 15 is disposed outside of the optical pumping magnet 17 as shown in FIG. 1, it is necessary for the optical pumping magnet 17 to be optically transparent in order to make the light that has emerged from the optical pumping excitation light source 15 pass through the optical pumping magnet 17 and reach the hyperpolarized noble gas generating cell 14. In this case, the direction in which the lines of magnetic force pass through the hyperpolarized noble gas generating cell 14 is approximately the same as the direction in which the light that has emerged from the optical pumping excitation light source 15 enters the hyperpolarized noble gas generating cell 14.

In this embodiment, the optical pumping excitation light source 15 is disposed outside of the optical pumping magnet 17. However, it is also possible to dispose the optical pumping excitation light source 15 on a lateral side of the hyperpolarized noble gas generating cell 14 and on an axis perpendicular to the lines of magnetic force of the optical pumping magnets 17, 17 so that the direction in which the lines of magnetic force pass through the hyperpolarized noble gas generating cell 14 is approximately perpendicular to the incident direction of the light. In such a case, because the direction in which the gas flows through the hyperpolarized noble gas generating cell 14, the direction in which the lines of magnetic force pass through the hyperpolarized noble gas generating cell 14, and the direction in which light enters the hyperpolarized noble gas generating cell 14 are all mutually perpendicular, the hyperpolarizability can be further enhanced as the noble gas passes through.

The nuclear magnetic resonance measuring instrument 32 includes a nuclear magnetic resonance measuring magnets 22, 22 and an NMR detector 21. The NMR detector 21 is connected to the very fine capillary tube 20 so as to enable the hyperpolarized noble gas to be introduced therein. The nuclear magnetic resonance measuring magnets 22, 22 may be, for example, a superconducting magnet or a permanent magnet which generates a high magnetic field of about 0.2 to 21 T. The nuclear magnetic resonance measuring instrument 32 may be a known NMR measuring instrument.

In the present embodiment, a single RF coil is provided in the nuclear magnetic resonance measuring instrument 32. The NMR detector 21 detects the absorption (nuclear magnetic resonance absorption) of electromagnetic waves emitted by the RF coil which is absorbed by the object under measurement.

By using the very fine capillary tube 20 to supply the hyperpolarized noble gas, it is possible to suppress spin relaxation and to supply the hyperpolarized noble gas even though the supply distance is 1 to 30 m. This enables the hyperpolarized noble gas generating cell 14 and the nuclear magnetic resonance measuring instrument 32 to be installed at a considerable distance therebetween. As a result, the influence of the leakage magnetic field from the nuclear magnetic resonance measuring magnets 22, 22 on the hyperpolarized noble gas generating cell 14 can be reduced, enabling the production amount of the hyperpolarized noble gas in the hyperpolarized gas generating cell 14 to be enhanced and the intensity of the NMR signal to be increased.

Next, a method for producing hyperpolarized noble gas using the hyperpolarized noble gas generator 31 of this embodiment is described.

The noble gas serving as the feedstock is a gas composed of monatomic molecules which has a nuclear spin. Among such gases, the xenon isotope having a mass number of 129 ($^{129}$Xe) and the helium isotope having a mass number of 3 ($^{3}$He), both of which have nuclear spins with a spin quantum number of 1/2, are preferred. Hyperpolarization can also be induced in gases having nuclear spins with a spin quantum number of 3/2 or 5/2. However, in such cases, spin relaxation arises due to the nuclear quadrupole moment, thereby the hyperpolarized state is maintained for only a short time, which is not very useful. Also, $^{3}$He has a natural abundance ratio of 0.000138% and thus requires enrichment, whereas the natural abundance ratio of $^{129}$Xe is 26.44%, enabling it to be used without enrichment. Hence, in terms of cost and other considerations, the use of xenon gas is more preferred.

In the present embodiment, a xenon gas of 98% by volume is used which contains a small amount of nitrogen. The small amount of nitrogen gas functions as a quencher gas. When the alkali metal of the optical pumping medium is exited by irradiation with an exciting light and returns from the excited state to the ground state, it experiences a primary process involving return to the ground state with the spontaneous emission of energy and a secondary process involving return to the ground state by a non-radiative transition. Since the secondary process has a long relaxation time, by introducing a quencher gas, intermediate level energies of the alkali metal can be transited to the quencher gas, enabling the alkali metal to return to the ground state in a short time. A hyperpolarized noble gas can also be produced without containing any such quencher gas whatsoever.

Examples of the quencher gases that may be used include inorganic gases such as hydrogen or nitrogen, and organic gases having an unsaturated bond, such as acetylene, benzene and π electron system compounds. Among these, nitrogen gas is preferred. The content of quencher gas varies as appropriate in accordance with the noble gas and the alkali metal used, but is preferably 80 vol % or less. In order to prevent oxidation of the alkali metal, it is preferable to minimize the content of water and oxygen as impurities in the noble gas and the quencher gas.

Illustrative examples of the alkali metals that may be used as the optical pumping medium include cesium (Cs), rubidium (Rb) and sodium (Na). "Optical pumping medium" refers herein to a substance for which, when an electron at the ground state level becomes excited by light absorption from irradiation using circularly polarized excitation light, jumps to an excited state level, and then returns to the ground state level, there is a high probability of transition to one of the electron levels among the ground state levels of which degeneracy has been magnetically broken by an externally applied magnetic field, thereby creating a state of high electron spin polarization. Among the above substances, rubidium which has a high vapor pressure is preferred from the standpoint that the optical pumping medium is vaporized to supply by drawing a vacuum within the hyperpolarized noble gas generating cell 14.

With regard to the wavelength of the optical pumping excitation light source 15, the excitation wavelength depends on the type of alkali metal to be used. For example, in the case in which rubidium is used, the center wavelength is preferably from 794.5 to 795.1 nm.

The output of the optical pumping excitation light source 15 may be adjusted in accordance with the size of the hyperpolarized noble gas generating cell 14 and the flow rate of the noble gas. However, a high output is preferred for hyperpolarizing all the noble gas within the hyperpolarized noble gas generating cell 14. An output of 10 to 200 W is more preferred.

In order to produce the hyperpolarized noble gas, the alkali metal serving as the optical pumping medium is introduced to the hyperpolarized noble gas generating cell 14, and then a noble gas is introduced. Thereafter, laser light is irradiated so as to effect hyperpolarization.

First, a commercially available glass ampule which encapsulates therein the alkali metal is placed within the alkali metal storage container 10. A first valve 7 and the gate valve 18 are closed, and then the second valve 8 is opened, and a vacuum is drawn on the interior of the hyperpolarized noble gas generating cell 14 using a vacuum pump 9. At this time, the guiding glass tube 19 and the very fine capillary tube 20 is removed, and the gate valve 18 is closed.

Next, while leaving the second valve 8 open, the alkali metal storage container 10 is gripped from outside with a clamp or the like and the glass ampule at the interior is broken, in addition to which the gas encapsulated within the glass ampule is drawn out by the vacuum and removed. Next, the gate valve 18 is opened and the vacuum pump connected to the bottom end 41 of the gate valve 18 is also used to evacuate a line on a downstream side of the hyperpolarized noble gas generating cell 14. The alkali metal storage container 10 is heated at 200 to 250° C. using a heater or the like so as to vaporize the alkali metal, and the vaporized alkali metal is transferred under a vacuum to the hyperpolarized noble gas generating cell 14. The alkali metal is deposited by cooling the bottom surface of the hyperpolarized noble gas generating cell 14 with an airflow of room temperature.

After the transfer of the alkali metal is complete, the second valve 8 and the gate valve 18 are closed, and the vacuum discharge of gases is stopped. Along with this, the temperature of the alkali metal storage container 10 is lowered to room temperature. And then, the first valve 7 is opened, thereby introducing from the noble gas cylinder 2 a high-purity noble gas as the feedstock for the hyperpolarized noble gas. When the pressure at the interior of the hyperpolarized noble gas generating cell 14 has become slightly higher than atmospheric pressure, the gate valve 18 is opened and the noble gas serving as the feedstock is continuously passed through at a flow rate controlled by the mass flow controller 3.

Next, the guiding glass tube 19 and the very fine capillary tube 20 are inserted into the protective line 40, and the very fine capillary tube 20 and the nuclear magnetic resonance measuring instrument 32 are connected. Then, the noble gas is supplied at a flow rate adjusted to 5 to 100 sccm, preferably 10 to 30 sccm, and most preferably 15 sccm. In this state, the furnace 45 is heated to 100 to 250° C., and preferably 220° C., laser light is irradiated from the optical pumping excitation light source 15, and a magnetic field is applied using the optical pumping magnets 17, 17. Thereby, a hyperpolarized noble gas is generated.

By setting the flow rate of the noble gas in a range of 5 to 100 sccm, it is possible to supply the hyperpolarized noble gas to the nuclear magnetic resonance measuring instrument 32 at about the same rate as the generation rate at which it is produced within the hyperpolarized noble gas generating cell 14. Hence, the hyperpolarized noble gas does not remain within the hyperpolarized noble gas generating cell 14, thereby, occurrence of spin relaxation due to collisions with the inside wall can be minimized. Also, because the hyperpolarized noble gas thus generated can be supplied as a laminar flow within the very fine capillary tube 20, the occurrence of spin relaxation due to collisions with the inside wall of the very fine capillary tube 20 can also be suppressed.

Next, the hyperpolarized noble gas which has been produced is supplied from the very fine capillary tube 20 to the nuclear magnetic resonance measuring instrument 32, and the NMR signal intensity is measured.

In the present embodiment, a flow-type cell which hyperpolarizes the noble gas as it passes through is used as the hyperpolarized noble gas generating cell 14 so as to enable continuous supply of the hyperpolarized noble gas. Alternatively, the hyperpolarized noble gas may instead be supplied in batch form using a storage cell.

Next, the magnetic resonance imager of the present invention is described. Aside from including a magnetic resonance image measuring instrument instead of the nuclear magnetic resonance measuring instrument 32, the magnetic resonance imager has a configuration identical to that of the above-described nuclear magnetic resonance spectrometer 1. Moreover, other than additionally having a plurality of coils in order to generate a gradient magnetic field, the magnetic resonance image measuring instrument has the same construction as the above-described nuclear magnetic resonance measuring instrument 32. Since the magnetic resonance imager of the present invention includes the hyperpolarized noble gas generator 31, desirable effects similar to those realized by the above-described nuclear magnetic resonance spectrometer 1 can be achieved.

EXAMPLES

The present invention is illustrated more fully by the following examples; however, these examples are not intended to limit the invention.

Examples 1 and 2

Relationship between Flow Rate and NMR Signal Intensity

Using very fine capillary tubes made of fused silica and having an inside diameter of 0.53 mm (Example 1) or 0.25 mm (Example 2) and a length in each case of 1.2 m (fused silica capillary tubes made by GL Sciences, Ltd.), the NMR signal intensities were measured at hyperpolarized xenon gas flow rates of 5, 10, 15, 20, 25, 30, 35, 40, 45, 50, 55, 60 and 65 sccm.

The hyperpolarized noble gas generating cell was a tabular flow cell which was made of quartz and had a length of 7 cm and a width of 5 cm, and a gap in the interior of the hyperpolarized noble gas generating cell through which the gas flowed had a height of 1 mm. Quartz tubes having an inside diameter of 4 mm were connected to both ends of the hyperpolarized noble gas generating cell.

First, rubidium (Furuuchi Chemical Corporation; purity of 99.9%) was vaporized by heating to a temperature of 220° C., and then transferred to a hyperpolarized noble gas generating cell on which a vacuum of $10^{-4}$ Pa was drawn.

Next, a mixed gas composed of xenon of 98 vol % and nitrogen (Taiyo Nippon Sanso Corporation) was introduced to the hyperpolarized noble gas generating cell and irradiated with light having a wavelength of 794.7 nm, a half width of 3 nm, and an output of 60 W using a laser diode (manufactured by Coherent, Inc.; B1-79-40.0C-19-30). In addition, a magnetic field of $1.25 \times 10^{-2}$ T was applied to the hyperpolarized noble gas generating cell using a permanent magnet (Sumitomo Special Metals Co., Ltd.). The temperature of the hyperpolarized noble gas generating cell was set at 145° C.

Figure 3:
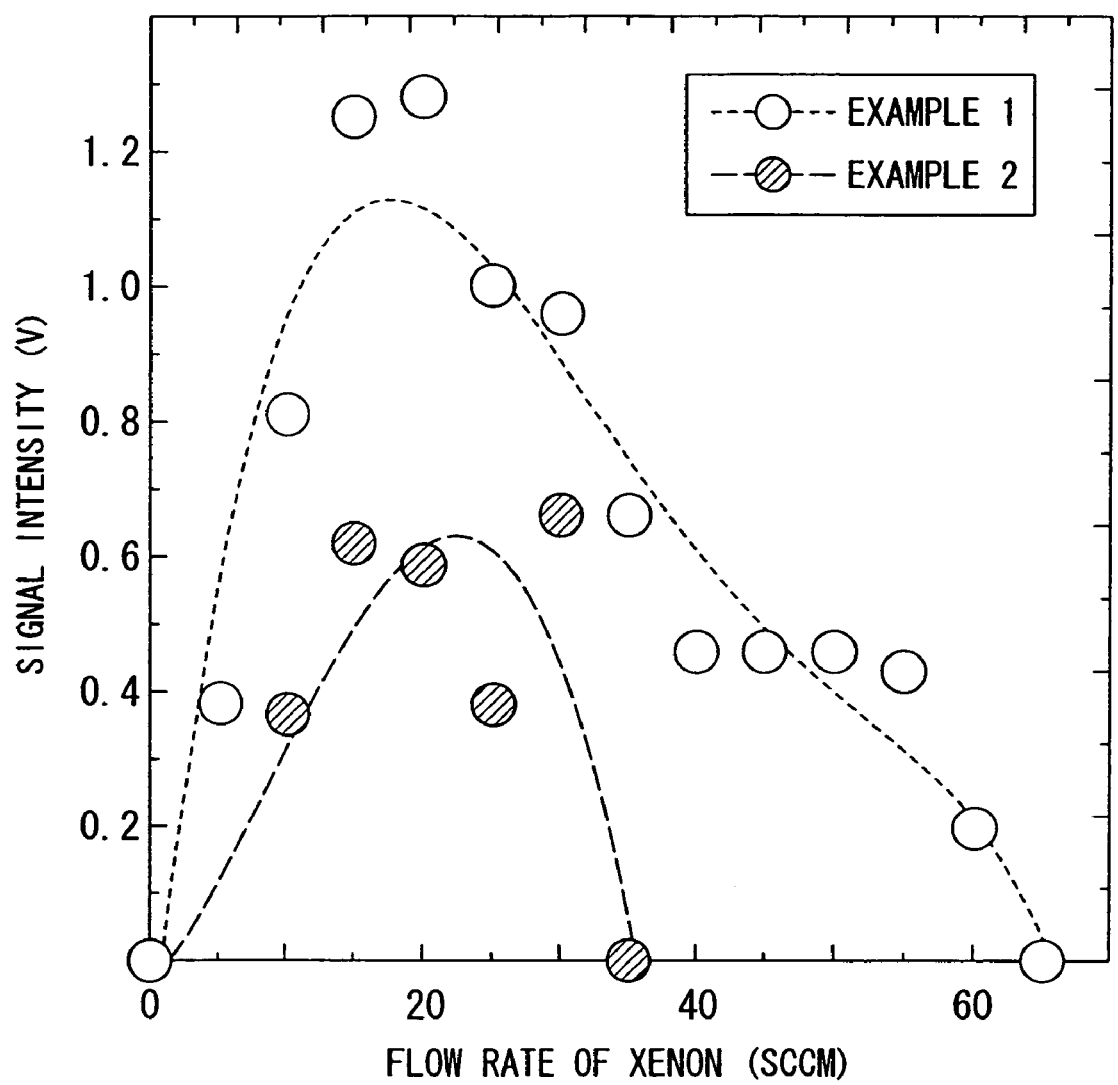
FIG. 3 is a graph showing the relationship between the flow rate of hyperpolarized xenon gas and the NMR signal intensity in Examples 1 and 2 of the present invention.

The intensity of the NMR signals was measured using a pulsed NMR spectrometer (Thamway Co., Ltd.). The measurement conditions were a magnetic field of 0.3 T and a frequency of 3.574 MHz, and free induction decay (FID) signals were obtained after a single pulse was applied. FIG. 3 shows the relationship between the hyperpolarized xenon gas flow rate and the NMR signal intensity.

From the results in FIG. 3, it is apparent that the NMR signal intensity exhibited a maximum value near a flow rate of 20 sccm in both Example 1 and Example 2. Since the relationship between the flow rate and the NMR signal intensity is not much dependent on the inside diameter of the very fine capillary tube, the maximum generation rate at which hyperpolarized noble gas is generated in the hyperpolarized noble gas generating cell appears to correspond to about 20 sccm.

That is, when the flow rate is higher than 20 sccm, it appears that the NMR signal intensity is low because the generation rate in the hyperpolarized noble gas generating cell is failing to keep up, as a result of which gas that has not been hyperpolarized is also being supplied together with the hyperpolarized gas. On the other hand, the decrease in the NMR signal intensity at a flow rate below 20 sccm appears to be due to the retention of the hyperpolarized noble gas within the hyperpolarized noble gas generating cell, and the ensuing collisions with the inside wall.

Examples 3 and 4

Relationship Between Very fine Capillary Tube Length and NMR Signal Intensity

Figure 4:
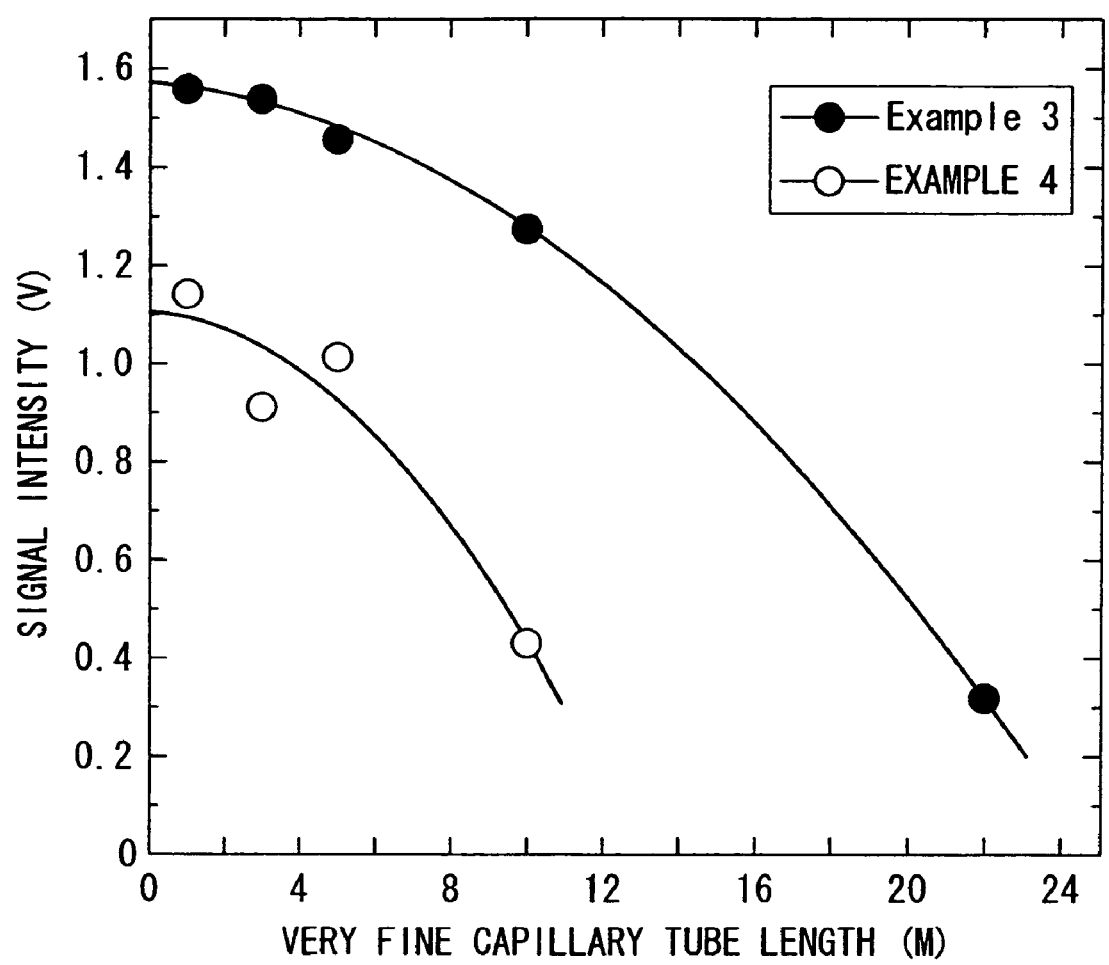
FIG. 4 is a graph showing the relationship between the length of the very fine capillary tube and the NMR signal intensity in Examples 3 and 4 of the present invention.
Figure 5:
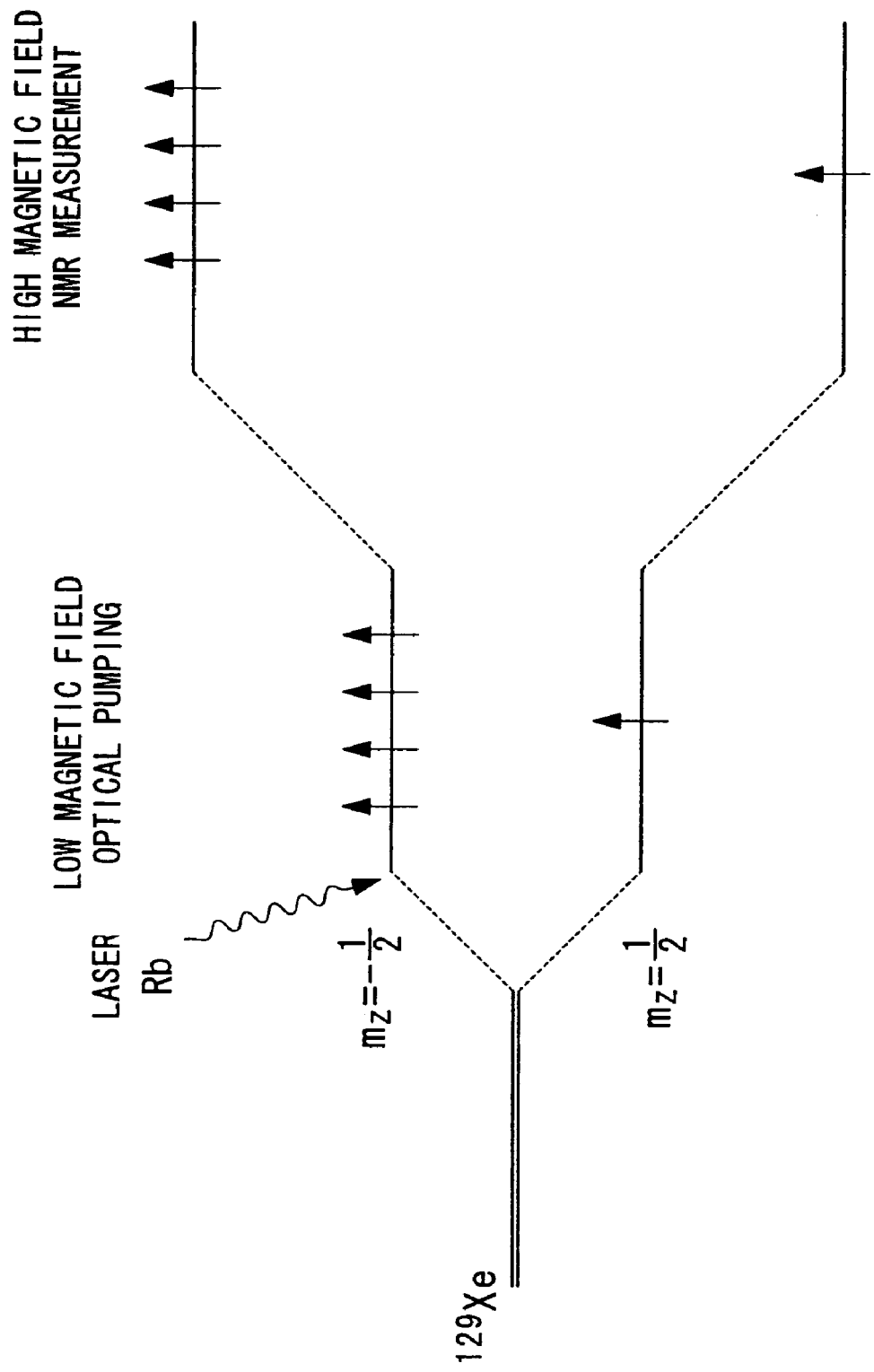
FIG. 5 is a model showing the relationship between the occurrence of difference in the number of occupied spin by the optical pumping of $^{129}$Xe and the energy level in NMR measurement.

Using very fine capillary tubes made of fused silica and having an inside diameter of 0.53 mm (Example 3, fused silica capillary tubes made by GL Sciences, Ltd.), the NMR signal intensity was measured at very fine capillary tube lengths of 1, 3, 5, 10 and 22 m, and a relationship between the flow rate and NMR signal intensity was determined at each very fine capillary tube length in the same manner as in Example 1. Table 1 below and FIG. 4 show the relationship between the very fine capillary tube length and the NMR signal intensity (maximum value).

Aside from using very fine capillary tubes having an inside diameter of 0.25 mm (Example 4) and setting the length of the tube to, variously, 1, 3, 5, or 10 m, the NMR signal intensity was measured in the same manner as in Example 3. Table 1 and FIG. 4 show the relationship between the very fine capillary tube length and the NMR signal intensity (maximum value).

TABLE 1

| | Signal intensity (V) | |
|---|---|---|
| Very fine capillary tube length (m) | Example 3 (internal diameter of 0.53 mm) | Example 4 (internal diameter of 0.25 mm) |
| 1 | 1.56 | 1.14 |
| 3 | 1.54 | 0.91 |
| 5 | 1.46 | 1.01 |
| 10 | 1.28 | 0.43 |
| 22 | 0.32 | — |

From the results in Table 1 and FIG. 4, it was confirmed in Example 3 that even at a very fine capillary tube length of 22 m, it was possible to observe and measure NMR signals. In Example 4, NMR signals were observed even at a length of 10 m. The relationship between the very fine capillary tube length and the NMR signal intensity was found to not depend very strongly on the inside diameter of the very fine capillary tube. Moreover, in both Examples 3 and 4, it was found that the NMR signal intensity tends to gradually decrease as the length of the very fine capillary tube increases.

Comparative Examples 1 and 2

Using a Pyrex (trademark) glass tube having an inside diameter of 4 mm and a length of 0.5 m for Comparative Example 1 and a Pyrex (trademark) glass tube having an inside diameter of 4 mm and a length of 1 m for Comparative Example 1, the NMR signal intensities were measured in the same manner as in Example 1 at a hyperpolarized xenon gas flow rate of 20 sccm. In Comparative Example 1, signals having an intensity of 1.4 V were observed. In Comparative Example 2, no signals were detected.

The above results demonstrate that the apparatus for producing a hyperpolarized noble gas of the present invention suppresses spin relaxation and can supply a hyperpolarized noble gas even over a long distance of 1 to 22 m.

Some preferred embodiments of the invention have been described above, although these embodiments are to be considered in all respects as illustrative and not limitative. Those skilled in the art will appreciate that various additions, omissions, substitutions and other modifications are possible without departing from the spirit and scope of the invention as disclosed in the accompanying claims.

What is claimed is:

1. An apparatus configured for producing a hyperpolarized noble gas which inhibits spin relaxation and avoids a decline in an NMR signal intensity of the hyperpolarized noble gas even when the gas is supplied over a long distance, comprising:
 a hyperpolarized noble gas generating cell in which a noble gas is subjected to an optical pumping in the presence of an alkali metal so as to generate a hyperpolarized noble gas; and
 a very fine capillary tube connected to the hyperpolarized noble gas generating cell and positioned downstream from the hyperpolarized noble gas generating cell, wherein the very fine capillary tube has an inside diameter of 0.1 mm to 1.22 mm and a length of 1 m to 22 m.

2. A nuclear magnetic resonance spectrometer which uses a hyperpolarized noble gas and avoids a decline in an NMR signal intensity of the hyperpolarized noble gas over a length of 1 m to 22 m comprising the apparatus configured for producing a hyperpolarized noble gas of claim 1 and a nuclear magnetic resonance measuring instrument which is supplied with hyperpolarized noble gas via the very fine capillary tube connected to the hyperpolarized noble gas generating cell.

3. A magnetic resonance imager which uses a hyperpolarized noble gas and avoids a decline in an NMR signal intensity of the hyperpolarized noble gas over a length of 1 m to 22 m comprising the apparatus for producing a hyperpolarized noble gas of claim 1 and a magnetic resonance image measuring instrument which is supplied with hyperpolarized noble gas via the very fine capillary tube connected to the hyperpolarized noble gas generating cell.

* * * * *